United States Patent
Capobianco et al.

(10) Patent No.: US 9,713,551 B2
(45) Date of Patent: Jul. 25, 2017

(54) KINESIOLOGY TAPE BANDAGE

(71) Applicant: Rocktape, Inc., Campbell, CA (US)

(72) Inventors: Steven Capobianco, Highlands Ranch, CO (US); Gregory van den Dries, Los Gatos, CA (US)

(73) Assignee: ROCKTAPE, INC., Campbell, CA (US)

( * ) Notice: Subject to any disclaimer, the term of this patent is extended or adjusted under 35 U.S.C. 154(b) by 0 days.

(21) Appl. No.: 14/659,835

(22) Filed: Mar. 17, 2015

(65) Prior Publication Data

US 2015/0328054 A1 Nov. 19, 2015

Related U.S. Application Data

(63) Continuation of application No. PCT/US2014/038438, filed on May 16, 2014.

(51) Int. Cl.
*A61F 13/00* (2006.01)
*A61F 13/02* (2006.01)

(52) U.S. Cl.
CPC ........ *A61F 13/0206* (2013.01); *A61F 13/022* (2013.01); *A61F 13/025* (2013.01); *A61F 13/0226* (2013.01); *A61F 13/0236* (2013.01); *A61F 2013/00238* (2013.01)

(58) Field of Classification Search
CPC .. A61F 13/02; A61F 13/0246; A61F 13/0289; A61F 13/0279; A61F 5/40
USPC ..... 523/105, 111, 112, 113, 114; 602/44, 52, 602/54, 55, 57, 58, 59, 903, 424; 428/175, 193, 196, 214
See application file for complete search history.

(56) References Cited

U.S. PATENT DOCUMENTS

| | | | |
|---|---|---|---|
| 4,727,868 A | 3/1988 | Szycher et al. | |
| 4,733,659 A | 3/1988 | Edenbaum et al. | |
| 4,780,168 A | 10/1988 | Beisang et al. | |
| 5,385,775 A | 1/1995 | Wright | |
| 5,861,348 A * | 1/1999 | Kase | A61F 13/025 428/195.1 |
| 5,921,948 A | 7/1999 | Kawaguchi et al. | |

(Continued)

FOREIGN PATENT DOCUMENTS

EP  2578734 A  4/2013
WO  2012156335 A  11/2012

OTHER PUBLICATIONS

"Viscose Rayon—the oldest man made fiber" (viscoserayon.PDF).*

(Continued)

*Primary Examiner* — Tarla Patel
*Assistant Examiner* — Caitlin Carreiro
(74) *Attorney, Agent, or Firm* — Young's Patent Services; Bruce A. Young

(57) ABSTRACT

A kinesiology tape bandage includes a piece of anisotropically stretchable woven fabric, a stretchable dressing attached to a first side of the fabric, and pressure-sensitive adhesive applied to at least some of an exposed area of the first side of the fabric. The kinesiology tape bandage is applied to a body by stretching the kinesiology tape bandage to at least 125% of its unstretched length, positioning a dressing of the bandage over a wound on the body, and pressing the stretched bandage against the body to activate a pressure-sensitive adhesive on the bandage and adhere the stretched bandage to the body.

16 Claims, 3 Drawing Sheets

(56) References Cited

U.S. PATENT DOCUMENTS

| | | | |
|---|---|---|---|
| 6,254,555 B1* | 7/2001 | Sevier | A61H 7/001 601/134 |
| 8,267,880 B2 | 9/2012 | Ritzdorf et al. | |
| 2002/0052570 A1* | 5/2002 | Naimer | A61F 13/0273 602/53 |
| 2003/0040691 A1 | 2/2003 | Griesbach et al. | |
| 2004/0044341 A1 | 3/2004 | Truckai et al. | |
| 2007/0254545 A1 | 11/2007 | Martin | |
| 2008/0014387 A1* | 1/2008 | Murphy | A61F 13/00991 428/34.1 |
| 2008/0264512 A1 | 10/2008 | Metzger | |
| 2009/0215924 A1* | 8/2009 | Zhu | A01N 25/04 523/122 |
| 2010/0018755 A1 | 1/2010 | Tatsuzawa et al. | |
| 2010/0298747 A1 | 11/2010 | Quinn | |
| 2011/0046526 A1* | 2/2011 | Evans | A61F 13/00017 602/3 |
| 2012/0232448 A1 | 9/2012 | Wuest | |
| 2015/0182384 A1 | 7/2015 | Case-Gustafson et al. | |

OTHER PUBLICATIONS

Korean Intellectual Property Office, International Search Report for PCT/US2014/0384738, Feb. 5, 2015.
Korean Intellectual Property Office, Written Opinion of the International Search Authority for PCT/US2014/0384738, Feb. 5, 2015.

* cited by examiner

KINESIOLOGY TAPE BANDAGE

CROSS-REFERENCE TO RELATED APPLICATIONS

This application is a continuation of International Patent Application PCT/US2014/038438 entitled "Kinesiology Tape Bandage" and filed on May 16, 2014, which is incorporated herein by reference in its entirety for any and all purposes.

BACKGROUND

Technical Field

The present subject matter relates to bandages, and more specifically, to bandages that have anisotropic stretch properties and include a dressing.

Background Art

It is well known that application of a bandage to cover a wound can accelerate the healing process. Many types of bandages are commonly used, including bandages with separate dressings and self-adhesive tape or non-adhesive elastic tape, and self-adhesive bandages with an integral dressing, such as Band-Aid® brand adhesive bandages from Johnson & Johnson, and a wide variety of other adhesive bandages in many different sizes using many different types of dressings to cover the wound. Dressings can be made of many different materials and can be absorbent or non-absorbent and in some cases are pre-treated with an antibiotic medicine.

Kinesiology tape, which is often a cloth-based self-adhesive tape, is a tape with anisotropic stretch properties, so that it is able to stretch much more in one direction, such as the length, than in the other direction, such as width. Traditionally, kinesiology tape is used to treat muscles and/or connective tissue that has been stressed in some way, but where there is no open wound. Kinesiology tape is applied to the individual in a stretched condition to provide a therapeutic benefit to the individual from the recoil effect of the elasticity of the tape. Kinesiology tape can be applied in many different configurations, depending on the tissue group being targeted and the intended effect, but in at least some situations, the tape is applied, in a stretched position, from the origin of the targeted muscle to the insertion point of the muscle. Once the tape has been applied, it is often rubbed to active a pressure-sensitive adhesive. While kinesiology tape is sometimes provided in pre-cut sections for specific taping patterns, it is often provided in a bulk form, such as a roll that allows for individual strips of tape to be cut to an appropriate length as needed.

BRIEF DESCRIPTION OF THE DRAWINGS

The accompanying drawings, which are incorporated in and constitute part of the specification, illustrate various embodiments. Together with the general description, the drawings serve to explain various principles. In the drawings.

DETAILED DESCRIPTION

Figures 1A, 1B, 1C:
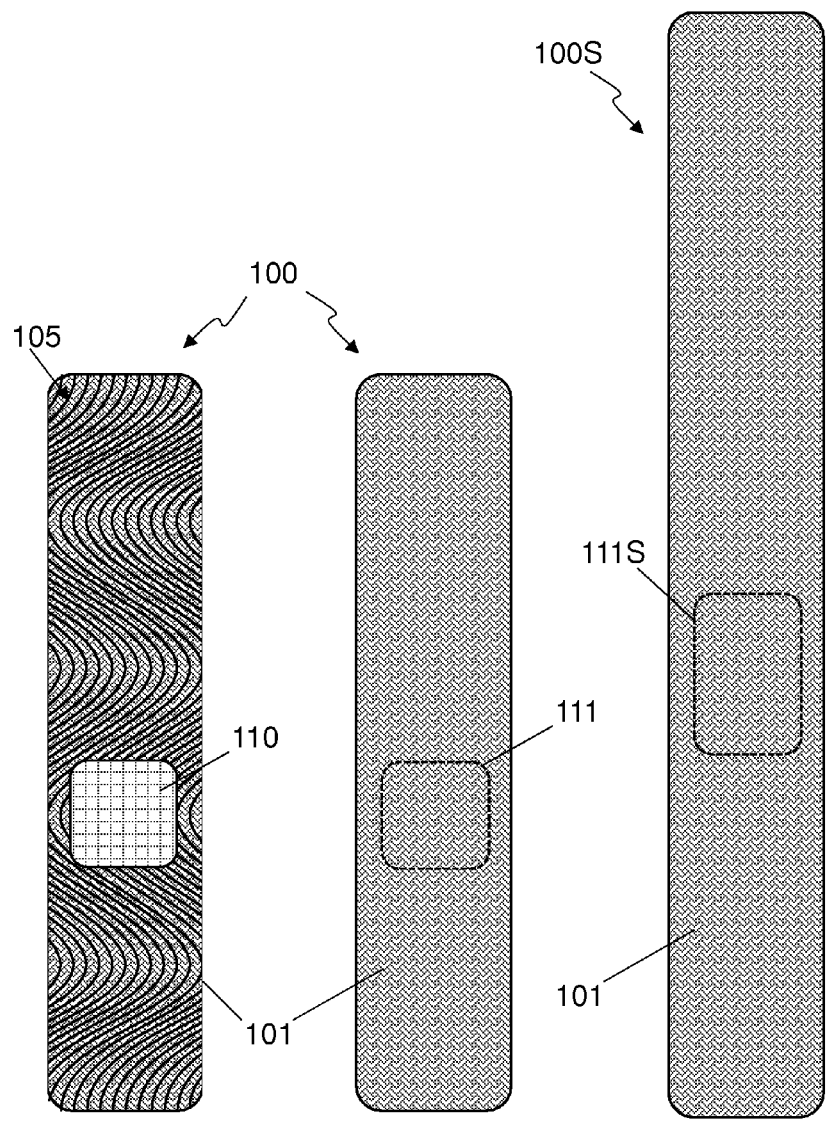
FIG. 1A shows the wound-facing side of an embodiment of a kinesiology tape bandage in an unstretched position.
FIG. 1B shows the non-wound-facing side of an embodiment of a kinesiology tape bandage in an unstretched position.
FIG. 1C shows the non-wound-facing side of an embodiment of a kinesiology tape bandage in a stretched position.

In the following detailed description, numerous specific details are set forth by way of examples in order to provide a thorough understanding of the relevant teachings. However, it should be apparent to those skilled in the art that the present teachings may be practiced without such details. In other instances, well known methods, procedures and components have been described at a relatively high-level, without detail, in order to avoid unnecessarily obscuring aspects of the present concepts. A number of descriptive terms and phrases are used in describing the various embodiments of this disclosure. These descriptive terms and phrases are used to convey a generally agreed upon meaning to those skilled in the art unless a different definition is given in this specification. Some descriptive terms and phrases are presented in the following paragraphs for clarity.

Kinesiology tape, as the term is used herein, refers to a woven fabric tape with anisotropic stretch qualities, so that the kinesiology tape can be stretched in one direction at least twice as much as in the orthogonal direction without significantly changing the unstretched dimensions of the kinesiology tape or its stretch attributes. An adhesive is affixed to one side of the kinesiology tape. The amount of stretch can vary between different brands of kinesiology tape, but any kinesiology tape can stretch to at least 125% of its unstretched length in its stretchable direction without a significant change in the unstretched length of the kinesiology tape after it returns to an unstretched state. The Rocktape™ brand of kinesiology tape can be stretched up to about 180% of its unstretched length. The direction of the kinesiology tape (or any anisotropically stretchable material) that can be stretched more than other directions may be referred to as the stretchable direction, even though the tape may allow some amount of stretch in the other directions. Kinesiology tape can be stretched in its non-stretchable direction, or the direction orthogonal to the stretchable direction, to a much lesser extent than its stretchable direction without impacting its unstretched dimensions, with a typical kinesiology tape stretchable only up to about 110% or less in the non-stretchable direction.

A dressing, as the term is used herein is material to be put in contact with a wound. The dressing is typically sterile, and may include an antibiotic in some embodiments. The dressing may be absorbent or non-absorbent, depending on the embodiment, and may be made with any type of material. Some embodiments of dressings may be configured in a way that they do not adhere to the wound.

The term "stretch" and its derivatives, as used herein, refers to lengthening a linear dimension of a material in a particular direction by applying a tensile force on the material in that direction. In some cases, other dimensions of the material may change, such as shorten, as the material lengthens in the stretch direction. As the term is used herein, once the tensile force on the material is removed, the material will return to about its original dimensions with no substantial change in the dimension of the material in the direction that the material was stretched. If the material does not return to about its original dimensions once the tensile force is removed, the material is deemed to have been overstretched instead of stretched.

A kinesiology tape bandage is a bandage made with a piece of kinesiology tape that includes a dressing affixed to the same side of the kinesiology tape as the adhesive. The kinesiology tape bandage can be made with any dimension and the dressing can be of any type and also be of any dimension. In many embodiments, the kinesiology tape bandage has a length that is significantly longer than its width, such as over twice as long as its width. In some embodiments, the length may have a dimension that is four times or more the dimension of the width.

The dressing of the kinesiology tape bandage is also stretchable, and may be anisotropically stretchable in some embodiments. In some embodiments, the dressing may include a porous, non-stick, stretchable membrane covering an absorbent filling. Depending on the embodiment, the dressing may include a woven material such as gauze, a foam material, a polyurethane film, or any other type of material. In at least one embodiment, a water-proof layer, that may also be virus-proof and/or bacteria-proof, is included in the dressing or positioned between the dressing and the kinesiology tape.

Reference now is made in detail to the examples illustrated in the accompanying drawings and discussed below.

FIG. 1A shows the wound-facing side of an embodiment of a kinesiology tape bandage 100 in an unstretched position. The bandage 100 includes a piece of anisotropically stretchable woven fabric 101 with a stretchable dressing 110 attached to the wound-facing side of the fabric 101. In at least some embodiment, the fabric 101 is breathable, allowing gasses and in some cases, fluids, to pass through the fabric 101. The fabric 101 may be woven from any type of fiber, but in at least one embodiment, the fabric 101 comprises 97% cotton and 3% Nylon 6/12. The fabric 101 may be identical to, or similar to, fabric used in one of many well-known brands of kinesiology tape, such as the Rocktape brand of kinesiology tapes.

A pressure-sensitive adhesive 105 is applied to at least some of an exposed area of the first side of the fabric. While some embodiments may fully coat the exposed areas of the wound-facing side of the fabric 101 with the pressure-sensitive adhesive 105, other embodiments apply the pressure-sensitive adhesive 105 in pattern of alternating adhesive and non-adhesive areas such as the wave pattern shown. Other embodiments may use other patterns including, but not limited to, lines or rectangular areas, dots or circles, or any other type of pattern. The adhesive may be hypoallergenic and/or latex-free, such as an acrylic adhesive, and may be water resistant in some embodiments, to allow the kinesiology tape bandage to remain adhered to a person's body even under moist or wet conditions, such as in a swimming pool or when the person is sweating heavily. In at least one embodiment, the woven fabric 101 and pressure-sensitive adhesive 105 are identical to those of one of the types of Rocktape brand kinesiology tape, such as the Rocktape Active Recovery (AR) tapes or the Rocktape H2O tapes.

The stretchable dressing 110 may be attached to the fabric 101 by any method, but in some embodiments, may be attached to the fabric 101 using the same adhesive 105 located under the dressing 110. In at least one embodiment, the dressing 110 is provided in a kit with a length of kinesiology tape made of the fabric 101 and the adhesive 105 and the dressing 110 is attached to the fabric 101 by pressing against the adhesive 105 at the time of application of the bandage 100.

The stretchable dressing 110 is often sterile, can be absorbent or non-absorbent, and may be made of any type of material, depending on the embodiment. In some embodiments, the stretchable dressing 110 may made using gauze and/or a foam material. In at least one embodiment, stretchable dressing 110 is made with porous, non-stick, stretchable membrane, such as a polyurethane film, covering an absorbent filling, to keep the dressing from sticking to the wound. The absorbent filling of the dressing 110 may include a woven material, a foam material, bonded materials, and/or loose materials held together by the membrane. In some embodiments, the absorbent filling of the dressing 110 includes at least one of acrylic fibers, polyester fibers, cotton fibers, or vicose fibers. In some embodiments, a water-proof layer, which may also be virus-proof and/or bacteria-proof, may be included between the fabric 101 and the dressing 110. This layer may be helpful to protect the wound and promote healing of the wound.

FIG. 1B shows the non-wound-facing side of an embodiment of a kinesiology tape bandage 100 in an unstretched position. FIG. 1B shows the opposite side of the bandage 100 of FIG. 1A. The bandage 100 can have any shape or size, including, but not limited to, substantially rectangular, substantially square, substantially round, substantially oval, substantially ellipsoid, a butterfly bandage shape, or any other regular or irregular shape. In some embodiments, sharp corners of the fabric 101 are rounded to reduce the possibility of the bandage 100 curling away from the body at the corners. In at least one embodiment, the bandage 100 has an unstretched length greater than four times its unstretched width, as shown. The location of the dressing 111 may or may not be visible from the non-wound-facing side, depending on the embodiment. In some embodiments the location of the dressing 111 may be marked on the fabric 101.

FIG. 1C shows the non-wound-facing side of an embodiment of a kinesiology tape bandage 100S in a stretched position. In the embodiment shown, the anisotropically stretchable woven fabric 101 has its stretchable direction aligned with the length of the bandage 100/100S. The piece of anisotropically stretchable woven fabric 100 in this embodiment is stretchable to at least 150% of a length of the fabric in a direction of the length, and stretchable to no more than 110% of width of the fabric in a direction of the width. So after being stretched the bandage 100 of FIG. 1B has a length that is half again as long, as shown by bandage 100S of FIG. 1C. In some embodiments, the piece of anisotropically stretchable woven fabric 101 is stretchable to at least 180% of a dimension of the fabric in one direction, such as the length of the bandage 100.

In at least some embodiments, the stretchable dressing 111 is stretchable in at least one direction by at least as great a percentage as the anisotropically stretchable woven fabric 101 in its stretchable direction. So in the stretched bandage 100S, the dressing 111S is also stretched. In at least one embodiment, the stretchable dressing 110 is anisotropically stretchable, and the stretchable direction of the stretchable dressing 110 is aligned with the length of the fabric 101, which is the stretchable direction of the fabric 101, wherein the length of the fabric 101 is longer than a width of the fabric.

Figure 2A:
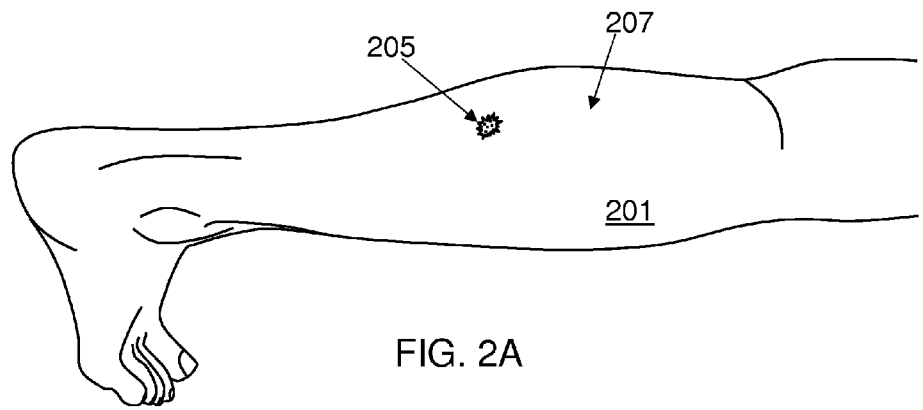
FIG. 2A shows an example wound on a human leg.

FIG. 2A shows an example wound 205 on a human leg 201. The human leg 201 is used as an example, but any part of a body of a living creature may be used. The wound 205 can be any type of wound, but may be an open wound where healing could be impacted by physical abrasion on the wound 205 or introduction of dirt or bacteria into the wound, or where an infectious agent, such as a bacteria or virus, could enter the body. In some cases, the wound 205 may be dry, but in other cases, bodily fluids may be present in the wound 205. The wound 205 could be the result of an externally inflicted injury to the skin of the leg 201, such as a cut or abrasion, or could be a sore generated by an internal condition, such as a boil or an infection.

In the example shown, a portion 207 of the body near the wound 205 is identified for treatment with kinesiology tape. The portion 207 may be identified due to an injury to the leg 201, such as a torn muscle, a sprain, or a strain, overuse of a muscle in the portion 207 causing pain, stiffness, or reduced strength, or due to a desire to improve athletic performance using the portion 207 of the leg 201, such as running speed. Any method of identifying a portion 207 of the body near the wound may be used. In the example shown, a muscle in the portion 207 having an injury is identified for treatment with kinesiology tape.

Figure 2B:
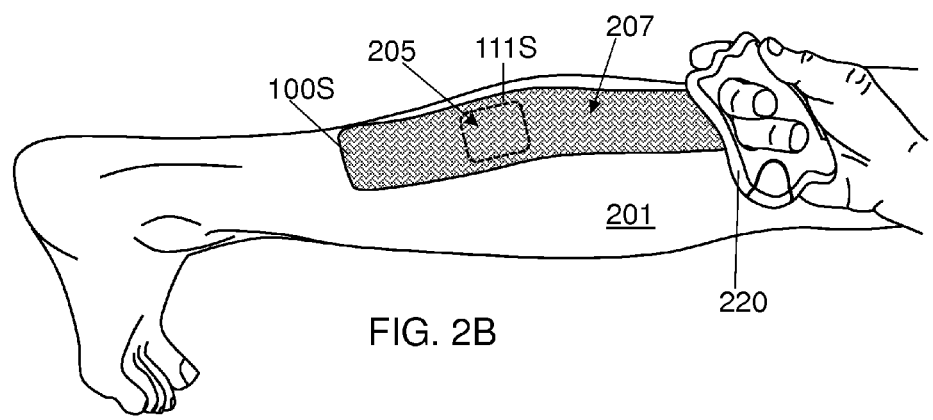
FIG. 2B shows an embodiment of a kinesiology tape bandage used to cover the wound and treat a muscle on the human leg.

FIG. 2B shows an embodiment of a kinesiology tape bandage 100S used to cover the wound 205 and treat a muscle 207 on the human leg 201. An anisotropically stretchable bandage 100S is applied to the leg 201 by stretching the anisotropically stretchable bandage 100S to at least 125% of its unstretched length, and positioning a dressing 111S of the bandage over a wound 205 on the leg 201. Because a muscle in the portion 207 of the body near the wound 205 was identified for treatment with kinesiology tape, the bandage 100S is applied over the identified portion 207 to allow the kinesiology tape bandage 100S to provide a therapeutic effect to the muscle. In at least one embodiment, the bandage 100S is positioned with one end of the bandage 100S at the origin of muscle, or where the muscle is attached to an immovable bone, and the opposite end of the bandage 100S is positioned at the insertion point of the muscle, or where the muscle is attached to a movable bone.

The stretched bandage 100S is then pressed against the leg 201 to activate a pressure-sensitive adhesive on the bandage 100S and adhere the stretched bandage 100S to the leg 201. In some cases, at least some portion of the bandage 110S is rubbed with a massage tool 220 to help activate the pressure sensitive adhesive and to massage a portion of the leg 201 covered by the bandage 100S. The massage of the portion 207 of the leg 201 with the massage tool 220 may also offer a therapeutic effect to the injured muscle.

Figure 3:
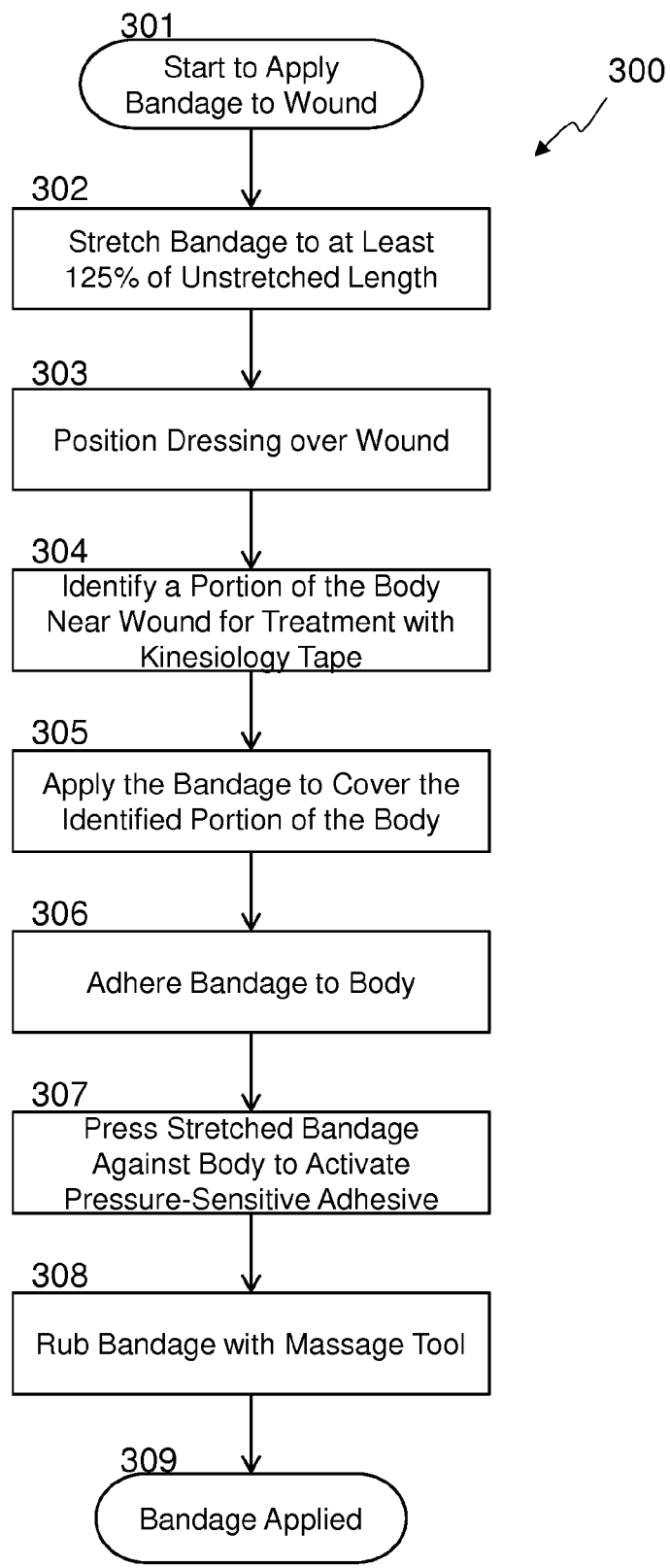
FIG. 3 shows a flowchart of an embodiment of a method of applying a kinesiology tape bandage to a body.

FIG. 3 shows a flowchart 300 of an embodiment of a method of applying a kinesiology tape bandage to a body. The flowchart 300 begins at block 301 by starting to apply a bandage to a wound. The method of applying an anisotropically stretchable bandage to a body includes stretching the anisotropically stretchable bandage to at least 125% of its unstretched length at block 302. In some embodiments, the bandage is stretched to between 130% and 150% of its unstretched length. In at least one embodiment, the bandage is stretched to about 180% of its unstretched length. In some embodiments where the dressing and the anisotropically stretchable tape are provided separately in a kit, the dressing may be applied to the anisotropically stretchable tape either before or after the tape is stretched. At block 303, a dressing of the bandage is positioned over a wound on the body.

In some embodiments, a portion of the body near the wound is optionally identified for treatment with kinesiology tape at optional block 304. If a portion of the body near the wound was identified for treatment with kinesiology tape, the bandage is applied at block 305 in such a way to provide treatment to the identified portion of the body. If no portion of the body near the wound was identified for treatment with kinesiology tape, the bandage may be applied in a way to best position the dressing to cover the wound. The bandage is then adhered to the body as positioned at block 306 so that the dressing covers the wound and, optionally, the kinesiology tape of the bandage can provide a therapeutic benefit to the identified portion of the body. The stretched bandage is then pressed against the body to activate a pressure-sensitive adhesive on the bandage at block 307. In some cases, at least some portion of the bandage may be optionally rubbed with a massage tool at block 308 to help activate the pressure sensitive adhesive and to massage a portion of the body covered by the bandage. The bandage has been successfully applied at block 309.

It should also be noted that, in some alternative implementations, not all the activities shown are performed and/or the activities noted in the block may occur out of the order noted in the flowchart 300. For example, activities described in two separate blocks may, in fact, be performed substantially concurrently, or the activities described in two separate blocks may be executed in the reverse order. It will also be noted that each block may be performed by one individual, or by different individuals in any combination.

Examples of various embodiments are described in the following paragraphs:

An example bandage includes a piece of anisotropically stretchable woven fabric, a stretchable dressing attached to a first side of the fabric, and pressure-sensitive adhesive applied to at least some of an exposed area of the first side of the fabric. In some example bandages, the piece of anisotropically stretchable woven fabric is stretchable to at least 150% of a dimension of the fabric in a first direction, and stretchable to no more than 110% of a dimension of the fabric in a direction orthogonal to the first direction. In some example bandages, the piece of anisotropically stretchable woven fabric is stretchable to at least 180% of the dimension of the fabric in the first direction. In some example bandages, an unstretched length of the piece of fabric is greater than four times an unstretched width of the piece of fabric. In some example bandages, the stretchable dressing is stretchable in at least one direction by at least as great a percentage as the anisotropically stretchable woven fabric in its stretchable direction. In some example bandages, the stretchable dressing comprises gauze. In some example bandages, the stretchable dressing comprises a foam material. In some example bandages, the stretchable dressing comprises porous, non-stick, stretchable membrane covering an absorbent filling. In some example bandages, the absorbent filling comprises a woven material. In some example bandages, the absorbent filling comprises at least one of acrylic fibers, polyester fibers, cotton fibers, or vicose fibers. Some example bandages also include a water-proof layer between the fabric and the dressing. In some example bandages, the water-proof layer is also virus-proof and bacteria-proof. In some example bandages, the stretchable dressing is anisotropically stretchable, and a stretchable direction of the stretchable dressing is aligned a stretchable direction of the fabric. In some example bandages, the pressure-sensitive adhesive is applied in a wave pattern to at least some of the exposed area of the first side of the fabric. Any combination of the examples of this paragraph may be used in embodiments.

An example method of applying an anisotropically stretchable bandage to a body includes stretching the anisotropically stretchable bandage to at least 125% of its unstretched length, positioning a dressing of the bandage over a wound on the body, and pressing the stretched bandage against the body to activate a pressure-sensitive adhesive on the bandage and adhere the stretched bandage to the body. Some example methods also include rubbing at least some portion of the bandage with a massage tool to help activate the pressure sensitive adhesive and to massage a portion of the body covered by the bandage. In some example methods the stretching comprises stretching the anisotropically stretchable bandage to between 130% and 150% of its unstretched length. Some example methods also include identifying a portion of the body near the wound for treatment with kinesiology tape, and applying the bandage to provide treatment to the identified portion of the body. In some example methods, the applying the bandage includes positioning one end of the bandage at the origin of a muscle in the identified portion of the body, and positioning an opposite end of the bandage at the insertion point of the muscle. In some example methods a muscle in the identified portion of the body has an injury.

The description of the various embodiments provided above is illustrative in nature and is not intended to limit the invention, its application, or uses. Thus, different variations beyond those described herein are intended to be within the scope of the embodiments of the present invention. Such variations are not to be regarded as a departure from the intended scope of the present invention. As such, the breadth and scope of the present invention should not be limited by the above-described exemplary embodiments, but should be defined only in accordance with the following claims and equivalents thereof. Any combination of the examples of this paragraph may be used in embodiments.

Unless otherwise indicated, all numbers expressing quantities of elements, optical characteristic properties, and so forth used in the specification and claims are to be understood as being modified in all instances by the term "about." Accordingly, unless indicated to the contrary, the numerical parameters set forth in the preceding specification and attached claims are approximations that can vary depending upon the desired properties sought to be obtained by those skilled in the art utilizing various principles of the present disclosure. Recitation of numerical ranges by endpoints includes all numbers subsumed within that range (e.g. 1 to 5 includes 1, 2.78, π, and 5). As used in this specification and the appended claims, the singular forms "a", "an", and "the" include plural referents unless the content clearly dictates otherwise. Thus, for example, reference to an element described as "an opening" may refer to a single opening, two opening, or any other number of openings. As used in this specification and the appended claims, the term "or" is generally employed in its "and/or" inclusive sense, which includes the case where all the elements are included, unless the content clearly dictates otherwise. As used herein, the term "coupled" includes direct and indirect connections. Moreover, where first and second devices are coupled, intervening elements including active elements may be located there between. Any element in a claim that does not explicitly state "means for" performing a specified function, or "step for" performing a specified function, is not to be interpreted as a "means" or "step" clause as specified in 35 U.S.C. §112(f).

The description of the various embodiments provided above is illustrative in nature and is not intended to limit the present invention, its application, or uses. As such, the breadth and scope of the present invention should not be limited by the above-described embodiments, but should be defined only in accordance with the following claims and equivalents thereof.

What is claimed is:

1. A bandage comprising:
   a piece of anisotropically stretchable woven fabric;
   a stretchable dressing attached to a first side of the fabric; and
   pressure-sensitive adhesive applied to at least some of an exposed area of the first side of the fabric;
   wherein the piece of anisotropically stretchable woven fabric is stretchable to a total stretched dimension of at least 150% of a first unstretched dimension of the fabric in a first direction, and stretchable to a total stretched dimension of no more than 110% of a second unstretched dimension of the fabric in a second direction orthogonal to the first direction.

2. The bandage of claim 1, wherein the piece of anisotropically stretchable woven fabric is stretchable to at least 180% of the first unstretched dimension of the fabric in the first direction.

3. The bandage of claim 1, wherein an unstretched length of the piece of fabric is greater than four times an unstretched width of the piece of fabric.

4. The bandage of claim 1, wherein the stretchable dressing is stretchable in at least one direction by at least as great a percentage as the anisotropically stretchable woven fabric in its stretchable direction.

5. The bandage of claim 1, wherein the stretchable dressing comprises gauze.

6. The bandage of claim 1, wherein the stretchable dressing comprises a foam material.

7. The bandage of claim 1, wherein the stretchable dressing comprises a porous, non-stick, stretchable membrane covering an absorbent filling.

8. The bandage of claim 7, wherein the absorbent filling comprises a woven material.

9. The bandage of claim 7, wherein the absorbent filling comprises at least one of acrylic fibers, polyester fibers, cotton fibers, or vicose fibers.

10. The bandage of claim 1, further comprising a waterproof layer between the fabric and the dressing.

11. The bandage of claim 10, wherein the water-proof layer is also virus-proof and bacteria-proof.

12. The bandage of claim 1, wherein the stretchable dressing is anisotropically stretchable, and a stretchable direction of the stretchable dressing is aligned with a stretchable direction of the fabric.

13. The bandage of claim 1, wherein the pressure-sensitive adhesive is applied in a wave pattern to at least some of the exposed area of the first side of the fabric.

14. The bandage of claim 1, wherein the pressure-sensitive adhesive is applied over a large enough portion of the exposed area of the first side of the fabric to adhere the bandage to skin of a human subject.

15. The bandage of claim 1, wherein the pressure-sensitive adhesive is applied in a pattern over substantially all of the exposed area of the first side of the fabric to adhere the bandage to skin of a human subject.

16. The bandage of claim 1, wherein the pressure-sensitive adhesive is adapted to be activated to stick to human skin by rubbing the bandage with a massage tool after the bandage is applied to a human subject.

* * * * *